United States Patent [19]

Kroneis et al.

[11] Patent Number: 5,185,263
[45] Date of Patent: Feb. 9, 1993

[54] METHOD FOR CALIBRATION OF A MEASUREMENT APPARATUS

[75] Inventors: Herbert Kroneis, Graz; Hermann Marsoner, Steinberg; Taghi Noormofidi, Graz, all of Austria

[73] Assignee: AVL Medical Instruments AG, Schaffhausen, Switzerland

[21] Appl. No.: 785,878

[22] Filed: Nov. 4, 1991

Related U.S. Application Data

[63] Continuation of Ser. No. 259,747, Oct. 19, 1988, abandoned.

[30] Foreign Application Priority Data

Oct. 23, 1987 [AT] Austria ............... 2816/87

[51] Int. Cl.⁵ .................................. G01N 31/00
[52] U.S. Cl. ............................ 436/8; 436/17; 436/50; 73/1 R
[58] Field of Search ............... 436/8–18, 436/50; 73/1 K

[56] References Cited

U.S. PATENT DOCUMENTS

| | | | |
|---|---|---|---|
| 1,919,858 | 7/1933 | Pettingill | 435/50 |
| 3,279,775 | 7/1981 | Louderback et al. | 436/11 |
| 4,163,734 | 8/1981 | Sorensen et al. | 436/18 |
| 4,299,728 | 11/1981 | Cormier | 436/11 |
| 4,424,276 | 1/1984 | Clark et al. | 436/50 |
| 4,843,013 | 6/1989 | Chiang | 436/18 |

FOREIGN PATENT DOCUMENTS 6343 10/1987 World Int. Prop. O. ............ 436/11

OTHER PUBLICATIONS

The Merck Index 10th Edition, Merck & Co. Inc, 1983 p. 1242.

Primary Examiner—James C. Housel
Assistant Examiner—William Chan
Attorney, Agent, or Firm—Watson, Cole, Grindle & Watson

[57] ABSTRACT

In order to calibrate a measurement apparatus used for determining at least the pH and $pCO_2$ values in aqueous media, two aqueous base solutions A and B with good storage stability are mixed at a defined ratio immediately prior to calibration, the desired pH and $pCO_2$ values being provided for calibration of the measuring electrodes of the measurement apparatus only after chemical reaction of the base solutions A and B has taken place.

17 Claims, 2 Drawing Sheets

METHOD FOR CALIBRATION OF A MEASUREMENT APPARATUS

This application is a continuation of application Ser. No. 259,747, filed Oct. 19, 1988 now abandoned.

BACKGROUND OF THE INVENTION

This invention relates to a method for calibration a measurement apparatus used for determining at least the pH and $pCO_2$ values in aqueous media, and to an arrangement for implementation of this method.

Because of the interdependence between the pH and $pCO_2$ values in aqueous media, a joint measurement of the two variables often is necessary in analytical chemistry. This applies in particular to biological systems in which $CO_2$ is to be evaluated as a metabolic product and the pH value as a state variable of the organism that is maintained constant within relatively narrow limits.

An analytical problem of this type is the analysis of blood gas, in which pH, $pCO_2$ and $pO_2$ values are obtained in undiluted blood. The new calibrating method will be described below using blood gas analysis as an example, to which it is in no way restricted, however.

DESCRIPTION OF THE PRIOR ART

Today various calibrating methods are used in blood gas analysis. For example, the gas sensors may be calibrated either by precisely standardized gas mixtures or by liquids equilibrated with gas mixtures at a constant temperature. In all instances the measuring or analyzing apparatuses must be provided with gas supply systems, either with precision equipment for gas-mixing according to Austrian Patent No. 300 423 and connections to bottles of compressed air and $CO_2$, for instance, or using suitable ready-for use precision gas mixtures directly supplied from the bottle.

Instead of compressed air, apparatuses with gas mixing equipment may also be operated with ambient air. A feeder line connecting to a $CO_2$ supply is indispensable, however.

The calibration partial pressures of $CO_2$ and $O_2$ usually are adjusted to their expected values in the sample; in blood gas analysis they are 40 and 80 mm Hg approximately (5.33 and 10.67 kPa) for $CO_2$, and O and 140 to 160 mm Hg approximately (0 and 18.67 to 21.33 kPa) for $O_2$.

For control purposes liquids may be employed that are sealed in suitable gas-tight containers and are equilibrated with precision gases. These systems have not been commonly accepted for calibrating purposes, however, and are designed for one-time applications rather than for repeated use, as the partial gas pressures will rapidly approach the values found in ambient air once the container has been opened.

For these reasons the known calibrating processes suffer from various disadvantages, such as the necessity to provide gas supply lines, high cost of precision gas mixing equipment and high demands with regard to gas-tight containers and connecting elements for the storage of equilibrated calibrating liquids.

Further requirements pertain to the specific sensors used, usually electro-chemical sensors, such as pH glass electrodes and Severinghouse $CO_2$ electrodes, i.e., membrane-coated glass electrodes in which pH changes in an electrolyte solution between membrane and glass electrode are caused by the activity of $CO_2$. In the instance of electrolyte losses or exsiccation, these sensors will lose their functionality, which means that they must be protected from drying out; for calibration by means of gases it is therefore demanded that these gases be saturated with water vapor.

For measuring of very small sample volumes — an important requirement not only in blood gas analysis — calibration by means of gaseous media is marked by yet another problem: the analyte volumes provided for interaction with the sensors are different for calibration and measurement, which may lead to differences in calibrated and measured values for one and the same analyte content, depending on the quality of the sensors.

SUMMARY OF THE INVENTION

It is the object of this invention to propose a method of calibration which avoids the above disadvantages and, above all, is independent of any external gas supply systems, and which protects the measuring elements and measuring electrodes to be calibrated from drying out, and which can also be used with measuring and analyzing equipment designed for measurement of very small sample volumes.

In the invention this object is achieved by mixing at a defined ratio two ageous base solutions of good storage stability, A and B, immediately preceding calibration, and by providing the desired pH and $pCO_2$ values for calibration of the measuring electrodes of the measurement apparatus only after chemical reaction of the base solutions A and B has taken place. The base solutions A and B may thus have pH and $pCO_2$ values which deviate considerably from the desired calibration values and remain stable even during storage of the solutions. The values required for calibration will arise only after the two base solutions A and B have been mixed at a defined ratio.

Both base solutions remain unaffected by exposure to air during storage, any possible influence being negligible for the quality of calibration. The critical value in this context is the $CO_2$ content of the base solutions, whose variation would change not only $CO_2$ but also pH calibration values.

As liquid calibrating media are used, no external gas supply systems and gas mixing equipment will be needed; besides, optimum protection of the measuring electrodes is ensured. The base solutions may be stored in conventional plastic containers, such as PVC or polyethylene bottles, temperature variations of $\pm 5°$ C. being admissible.

In a further development of the invention it is provided that the base solution A contain defined quantities of the acid component of a pH buffer system, and the base solution B defined quantities of carbonate and bicarbonate. The stability of the base solution A is thus given by its acid character, which permits only traces of $CO_2$ from the air to enter into solution, whereas the stability of the base solutions B is ensured by its $HCO_2^-/CO_3^{2-}$ buffer system.

Whether the base solution B can be obtained with or without the addition of a further alkaline component will depend on which calibration values are to be established. In certain instances the invention therefore provides that the base solution B additionally contain the alkaline component of the pH buffer system. While the base solution A contains the acid component of a buffer system, the solution B will contain in addition to bicarbonate and carbonate in pre-determined ratio the alkaline component of the buffer system.

In a further variant of the invention the proposal is put forward that in the base solution B a $pCO_2$ value be set resulting from the bicarbonate/carbonate ratio, which should correspond to the mean $pCO_2$ value of the ambient air. Particularly good stability against influences due to air and $CO_2$ is achieved by choosing the ratio between bicarbonate and carbonate — and thus the pH value — in accordance with the chemical equilibria between $CO_2$ ($H_2CO_3$), $HCO_3^-$ and $CO_3^{2-}$ in such a way that the solution has the same $CO_2$ value as the air:

In accordance with these equilibria the species $CO_2$, $HCO_3^-$ and $CO_3^{2-}$ can be made interconvertible by shifting the pH value. On the other hand, it is possible by a defined use of the non-volatile alkaline components $HCO_3^-$ and $CO_3^{2-}$ to force a pH value in the aqueous system at which the volatile component ($CO_2$) is hardly present.

The buffer system $HCO_3^-/CO_3^{2-}$ is now effective and will permit a pH value in the high pH range to be precisely predicted and set. This pH value may be selected such that the partial $CO_2$ pressure of the solution, given by the amount of the volatile component $CO_2$, will correspond to the partial $CO_2$ pressure of the ambient air.

The extent to which expected $pCO_2$ fluctuations in ambient air and temperature fluctuations of $\pm 5°$ C. will influence the $CO_2$ content of the base solution B is indicated in the estimate below:

(a) $pCO_2$ fluctuations in ambient air
assumptions: air-$CO_2$-partial pressure: $0.3 < pCO_2 < 0.6$ mm Hg
containers:
 500 ml PVC bottles
 500 ml polyethylene (PE) bottles
storage period: 1 year
results (worst case): 0.01% $CO_2$ (for PVC) and 0.02% $CO_2$ (for PE) of the total content of solution B is absorbed/released if the partial pressures indicated as limiting values (0.3 and 0.6 mm Hg) are active in the environment over a period of 1 year.

(b) In the case of temperature fluctuations of $\pm 5°$ C. about an assumed storage temperature of 25° C. the $CO_2$ contents will change over a storage period of 1 year as following (worst case, i.e., extreme temperatures):
PVC bottles: 0.006%
PE bottles: 0.011%

These worst case changes of the overall $CO_2$ content in solution B are negligible from a measurement point of view, and are smaller by a factor of 400 to 1200 than overall $CO_2$ changes of gas-equilibrated calibrating solutions with a $pCO_2$ value of 40 to 80 mm Hg under identical conditions.

The invention may further provide that pH inactive salts be added to the base solutions A and/or B in order to adapt the ionic strength to the sample, NaCl and/or KCl being used as pH inactive salts. It is possible to adjust the ionic strength of the two base solutions by the addition of one or several inert salts, such as NaCl, KCl, to any preselected level. This will be of advantage if the properties of the calibrating media are adapted to those of the sample. With this kind of adaptation differences in the diffusion potentials at the reference electrodes of the pH measurement set-up can be minimized, for instance, which — if neglected — would lead to differences in calibration and measurement results.

Suitable buffering agents whose acid component is applied in base solution A and whose alkaline component in base solution B, are all buffer systems with sufficient buffering capacity for calibration at the desired pH value to be calibrated. Especially for blood gas analyses with pH values of approximately 7 the invention provides that pH buffer system be selected from the group of phosphate buffers or of the water-soluble organic amino buffers. Suitable amino buffers are mops, hepes, tris, thriethanolamine, etc.

As has been stated before, the base solutions A and B have good storage stability. The storage stability of solution A depends largely on its specific pH level, for instance pH 5.5. The stability of solution B is determined by the buffer system $HCO_3^-/CO_3^{2-}$, by means of which pH values may be set, such that the solution has a definable partial $CO_2$ pressure. By mixing the solutions A and B the buffering capacity of the $HCO_3^{-2}/CO_3^{2-}$ system is lost, while the buffer system of the additional buffer components becomes effective. This buffer system in the mixture will provide the desired calibrating pH; a shift in the bicarbonate/carbonate equilibrium will lead to the preselected calibration partial pressure of $CO_2$ at the calibrating pH value.

A further development of the invention provides that at least a two point calibration be carried out, for which at least two different mixing ratios of the base solutions A,B should be chosen. The concentrations of the solution components may be chosen such that the desired calibration quantities, for example for blood gas analysis, are obtainable by two different mixing ratios, the two base solutions remaining the same. Common calibration values in blood gas analysis are: pH = 7.383 and 6.841, $pCO_2 = 40$ and 80 mm Hg, respectively.

Particular simplification is achieved if the mixing ratios chosen are, firstly, x:y and, secondly, y:x, for example, 1:2 and 2:1. In this way calibration measurement pairs are obtained simply by inverting the mixing ratio of the base solutions within the customary range of calibration values. Although not required by the calibrating method, the customary calibration values may be obtained with as great precision as desired if more complicated mixing ratios are selected.

For the mixing ratio A:B = 1:2 the chemical processes are described below.

Concentrations of participating components (weighed portion) in base solutions A and B
Solution A [HP] = feed concentration (e.g. mole/l) of buffer acid
Solution B
 [P$^-$] = feed concentration of buffer base
 [$HCO_3^-$] = feed concentration of bicarbonate
 [$CO_3^{2-}$] = feed concentration of carbonate
Concentrations in the mixture for a mixing ratio A:B = 1:2 and before chemical equilibrium has been established, are:

$$\tfrac{1}{3}[HP], \tfrac{2}{3}[P^-], \tfrac{2}{3}[HCO_3^-], \tfrac{2}{3}[CO_3^{2-}]$$

Establishment of chemical equilibrium:

Step 1: $HP + CO_3^{2-} \rightarrow P^- + HCO_3^-$

The carbonate present is reacted with part of the buffer acid. Resulting concentrations after step 1:

$[HP^*] = \frac{1}{3}[HP] - \frac{2}{3}[CO_3^{2-}]$ $[P^{-*}] = \frac{1}{3}[P^-] + \frac{2}{3}[CO_3^{2-}]$ $[HCO_3^{-*}] = \frac{2}{3}[HCO_3^-] + \frac{2}{3}[CO_3^{2-}]$ $[CO_3^{2-*}] = 0$ (negligible)

For instance, if the concentration of the buffer acid [HP] in the base solution A is 51 mmole/l, and the carbonate concentration $[CO_3^{2-}]$ is 9 mmole/l, the following concentrations prevail for a mixing ratio of A:B = 1:2 before the chemical equilibrium is established: $\frac{1}{3}[HP] = 17$ mmole/l and $\frac{2}{3}[CO_3^{2-}] = 6$ mmole/l. The concentration $HP^* = \frac{1}{3}[HP] - \frac{2}{3}[CO_3^{2-}]$ obtained after step 1 will be 11 mmole/l if a negligible $CO_3^{2-}$ concentration is assumed.

Step 2: $HF + HCO_3^- \rightarrow P^- + H_2CO_3 \ (= \alpha_{Co2}\cdot pCO_2)$

Another part of the buffer acid is reacted with bicarbonate. This reaction continues until equilibrium is reached, without completely using up any of the components, and may be quantified mathematically from the buffer equations for the buffer systems $HP/P^-$ and $H_2CO_3^-$:

$$pH = pK_{HP} + \log \frac{(P^{-*}) + x}{(HP^*) - x}$$

$$pH = pK_s + \log \frac{(HCO_3^{-*}) - x}{x} \quad x = \alpha_{CO2}\cdot pCO_2$$

From the two equations with two unknowns the pH and $pCO_2$ values of the mixture in equilibrium are obtained.

$pK_{HP}$: negative decadic logarithm of the dissociation constant of [HP]

$pK_S$: negative decadic logarithm of the "apparent dissociation constant" of carbonic acid $\alpha CO_2$: solubility coefficient of $CO_2$ The table below gives a comparison of feed concentrations of solution components and equilibrium concentrations after mixing of solutions A and B, for a mixing ratio of 1:2.

|  | concentrations in base solutions | concentrations in 1:2 mixture |
|---|---|---|
| buffer acid (HP) | [HP] in solution A | $\frac{1}{3}[HP] - \frac{2}{3}[CO_3^{2-}] - x$ |
| buffer base ($P^-$) | $[P^-]$ in solution B | $\frac{2}{3}[P^-] + \frac{2}{3}[CO_3^{2-}] + x$ |
| bicarbonate | $[HCO_3^-]$ in solution B | $\frac{2}{3}[HCO_3^-] + \frac{2}{3}[CO_3^{2-}] - x$ |
| carbonate | $[CO_3^{2-}]$ in solution B | approx. = 0 for pH = 7 |
| $H_2CO_3$ ($\alpha_{CO2}\cdot pCO_2$) }  pCO_2 | $pCO_2 = (pCO_2)$ air | $x = \alpha_{co2}\cdot pCO_2$ |

It is not essential that $[P^-]$ be entered, since the buffer base will form from the corresponding buffer acid in a defined amount due to the establishment of equilibrium upon mixing. Solution B may thus consist only of components $HCO_3^-$ and $CO_3^{2-}$ (in water).

In a preferred form of the invention it is proposed that a dye be added to one of the base solutions and that the mixing ratio of the base solutions be tested by means of optical methods, such as absorption measurements. The addition of a dye to one of the two base solutions provides a possibility of checking that is applicable to all types of mixing processes conceivable. The reduction in concentration in accordance with the mixing ratios may be determined in a flow cell, for example (Lambert-Beer Law). The possibility of an internal calibration by measuring the dyed mixture and the unmixed solutions is particularly advantageous in this context.

EXAMPLES

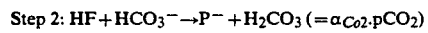

| composition mmole/l | | | | mixing ratio A:B | resulting calibration values | |
|---|---|---|---|---|---|---|
| Solution A | | Solution B | | | pH | pCO₂ |
| KH₂PO₄ | 51,5 | Na₂HPO₄ | 50,05 | 1:2 | 7,383 | 40,0 |
| NaCl | 20,0 | KHCO₃ | 27,65 | 2:1 | 6,709 | 82,1 |
| | | Na₂CO₃ | 8,40 | 3:2 | 6,832 | 77,8 |
| KH₂PO₄ | 23,8 | KHCO₃ | 25,3 | 1:2 | 7,383 | 36,8 |
| NaCl | 125,0 | Na₂CO₃ | 7,7 | 2:1 | 6,540 | 97,3 |
| | | NaCl | 110,0 | 1:1 | 6,865 | 81,0 |
| MOPS | | NaMoPS | 35,5 | 1:2 | 7,382 | 39,0 |
| (free | | KHCO₃ | 26,8 | 2:1 | 6,696 | 80,6 |
| acid) | 50,0 | Na₂CO₃ | 8,1 | 3:2 | 6,822 | 76,3 |
| NaCl | 100,0 | NaCl | 100,0 | | | |

It is also possible, of course, to add other chemical of physical markers to one of the base solutions, for instance fluorescence quenchers or radioactively labelled substances.

The table below indicates that deviations from the ideal calibration value in the instance of deviations from the ideal mixing ratio are very small in the calibrating method proposed by the invention.

| A:B (ideal) | pH (ideal) | pCO₂ (ideal) | mixing error | pH | pCO₂ |
|---|---|---|---|---|---|
| 1:2 | 7,382 | 38,46 | 0 | 0 | 0 |
| | | | 0,5% | <±0,004 | <0,21 mmHg |
| | | | 1,0% | <±0,007 | <0,41 mmHg |
| | | | 2,0% | <0,013 | <0,83 mmHg |
| 2:1 | 6,697 | 79,63 | 0 | 0 | 0 |
| | | | 0,5% | <0,003 | <0,06 mmHg |
| | | | 1,0% | <0,005 | <0,10 mmHg |
| | | | 2,0% | <0,010 | <0,20 mmHg |

In many analyses, above all in biological applications, the partial oxygen pressure $pO_2$ of the media to be analyzed also is of interest. The invention therefore proposes that one of the base solutions A and B be equilibrated with oxygen from the ambient air immediately before calibration, which also eliminates the necessity of an external gas supply line for oxygen; in addition to the pH and $pCO_2$ calibrations is to be performed.

According to the invention equilibration of the base solutions A or B with oxygen may be performed in a piece of silicone tubing between the particular storage container of the base solution and the corresponding measuring electrodes. Equilibration of the base solutions A or B of the $CO_2$/pH calibrating system with ambient air need not be performed under thermostatic conditions, but the equilibration process should be carried out under controlled temperature conditions, the temperature being raised to $T_M$ (measuring/calibrating temperature) without gas exchange.

$$(cO_2)_{T1} = a_{O2.T1} \cdot (pO_2) \text{ environment}$$

$$(pO_2)_{TM} = \frac{(cO_2)_{T1}}{a_{O2.TM}}$$

$$(pO_2) \text{ environmt.} = (p - p_{H2O.T1}) \cdot 0{,}209$$

$cO_2$: concentration of dissolved oxygen
$pO_2$: partial oxygen pressure
p: air pressure
$a_{O2}$: solubility coefficient of oxygen $a_{O2} = f(T)$
$T_1$: equilibration temperature
$pH_2O$: water vapor pressure It is also possible to perform the equilibration directly at the measuring temperature, for instance at 37° C., and to subject the solution to the thermostat control in accordance with this temperature.

Finally, the base solution A may be equilibrated with ambient air at temperatures >37° C. As the solubility of oxygen is temperature-independent, partial oxygen pressures smaller than the partial $O_2$ pressure of air may be attained for calibration processes at 37° C. For a $pO_2$ value of 155 mmHg for ambient air and equilibration at 43.5° C., a $pO_2$ value of 140.4 mmHg at 37° C. may be attained after cooling off to 37° C. without gas exchange.

Oxygen calibration may also be implemented by means of another liquid in the measurement apparatus, for instance by equilibrating the washing liquid with oxygen. A suitable site for the equilibration process would be a heated silicone tube containing an insulated heating wire and preferably carrying several temperature sensors that may be employed for control purposes.

The flow of ambient air for $O_2$ equilibration at the respective temperature may be saturated with water vapor in order to avoid changes in the concentration of the solution.

Furthermore, the base solution A can be equilibrated with ambient air directly in its storage tank, since due to the acid character of solution A no detectable effects on the $pH/pCO_2$ calibration system are to be expected.

If particular calibrating methods should require that the $pO_2$ zero point be included in the calibration, the invention proposes that the oxygen be removed from one of the base solutions (A or B) by a cathodic reaction. In a simple method of oxygen removal by electrochemical means a flow cell with large area cathodes is used, which is positioned in the transport path or in a bypass in front of the measuring chamber. The cathode may be configured as an uncoated platinum wire running along a piece of tubing or a pipe serving as an anode. Such a system functions in analogy to the polarographic oxygen electrodes. Upon application of a voltage cathodic oxygen reaction takes place, the current present during this process indicating the $O_2$ reaction rate at the cathode. This will permit either to control the completeness of the reaction or to stop the reaction before the oxygen is completely consumed and to employ the value of the electrical current as a measure for the remaining oxygen content. An internal calibration value of this system is given by the current at the beginning of the reaction of an air-equilibrated solution, for instance. This method will permit multiple point calibrations, an anaerobic transport to the measuring system is required, however.

According to the invention it is also possible that a solution C be used for calibrating the $pO_2$ zero point, preferably a washing solution which contains an oxygen reducing agent, for instance $Na_2SO_3$. Other such agents include sodium dithionite and pyrogallol in excess in aqueous solutions, by which molecular oxygen is reduced. As the above reactions take place in an alkaline environment tensides of a preferably non-ionic nature should be added to the solution C, which may be used as a washing liquid at the same time. In this context preference is given to $Na_2SO_3$, which will provide for a stable reaction product upon reaction with oxygen.

A possibility of testing for the absence of oxygen is provided by checking the oxygen content of the solution C used for calibration of the $pO_2$ zero point, by adding a redox indicator whose color will change upon transition from the oxidized to the reduced state. Suitable redox indicators are those with different colors in the oxidized and the reduced state. In the presence of the $O_2$-reducing substance the indicator is characterized by its reduced state, whereas it will change its color in the presence of $O_2$. Examples include pyrogallol as an indicator changing to brown upon reaction with $O_2$, and inorganic redox dyes.

A further possibility of testing for the $O_2$ content is provided by the invention: If $Na_2SO_3$ is used as an oxygen-reducing agent, the oxygen content of the solution C used for calibrating the $pO_2$ zero point can be checked by the addition of a pH indicator, which will undergo a change in color if the pH of solution C is shifted from 9 to 7. Testing for the absence of oxygen by means of $SO_3$ consumption is facilitated by the addition of a pH indicator with a color changeover point between pH=7 and pH=9, as the oxidation from sulfite to sulfate is accompanied by a shifting of the pH of the solution from pH~9 to pH~7. Such indicators are known from the pertinent literature, e.g. cresol red or neutral red.

In the invention an arrangement for implementation of the method proposed by the invention for calibration of a measurement/analyzing apparatus comprising a measuring element with measuring electrodes for determining the pH, $pCO_2$ and, if applicable, the $pO_2$ values, and further comprising containers for washing, calibrating and reference media, and a calibration device, is obtained by furnishing the calibration device with two or more storage containers for liquid base solutions A and B, and by providing a metering device for mixing the base solutions at a defined ratio before they enter the measuring element.

It will be of advantage for the invention if the metering device is followed by a mixing chamber which may be equipped with a mixing element, preferably a magnetic stirrer.

In a particularly simple variant of an arrangement according to the invention the metering device has two pieces of tubing of different cross-sections served by a pump, preferably a peristaltic pump, each of which is connected to a storage tank on the one side and to the mixing chamber on the other side.

For two-point calibrations, in which two mixed solutions are produced by inverting the mixing ratios of the two base solutions A and B, a preferred version of the invention proposes that three pieces of tubing be provided, preferably via a peristaltic pump, the first piece being connected to one of the storage containers and the other one to the second storage container, and the third piece of tubing being connectable to each of the containers in turn via a switching unit, all pieces leading into the mixing chamber. It is of particular advantage if the three pieces of tubing have identical cross-sections for establishing the mixing ratios 1:2 and 2:1.

Finally, it is proposed in another variant of the invention that the metering device be provided with a syringe for each of the base solutions A and B, the syringes connected to one storage container each having different plunger diameters or different lengths of stroke. Again, a mixing chamber may be positioned in front of the measuring element the analyzing apparatus.

BRIEF DESCRIPTION OF THE DRAWING

Following is a more detailed description of the invention as illustrated by the accompanying drawing, in which FIG. 1 gives a schematical view of an arrangement for implementation of the calibration method proposed by the invention.

DETAILED DESCRIPTION OF THE PREFERRED EMBODIMENTS

Figure 1:
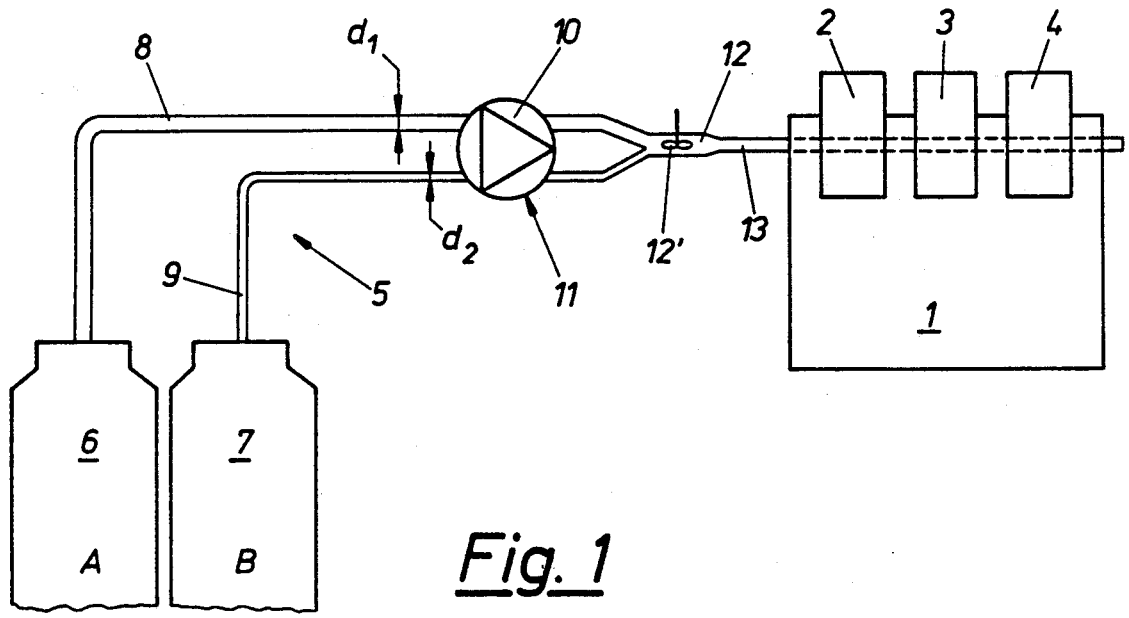

FIG. 1 shows a measuring/analyzing apparatus with a measuring element 1 containing measuring electrodes 2,3,4, for instance for pH, $CO_2$ and $O_2$ measurements. During calibration of the measurement apparatus by means of the calibration device 5, the base solutions A and B are conveyed from the storage containers 6,7 into a mixing chamber 12 via pieces of tubing 8,9 by means of the peristaltic pump 10, which is used as a metering device 11, and are then mixed, if necessary by a mixing element 12' located in the mixing chamber 12. The mixture is then conveyed via the piece of tubing 13 to the individual measuring electrodes 2,3,4 of the measuring element 1. The required mixing ratio is determined by cross-sections $d_1$ and $d_2$.

Figure 2:
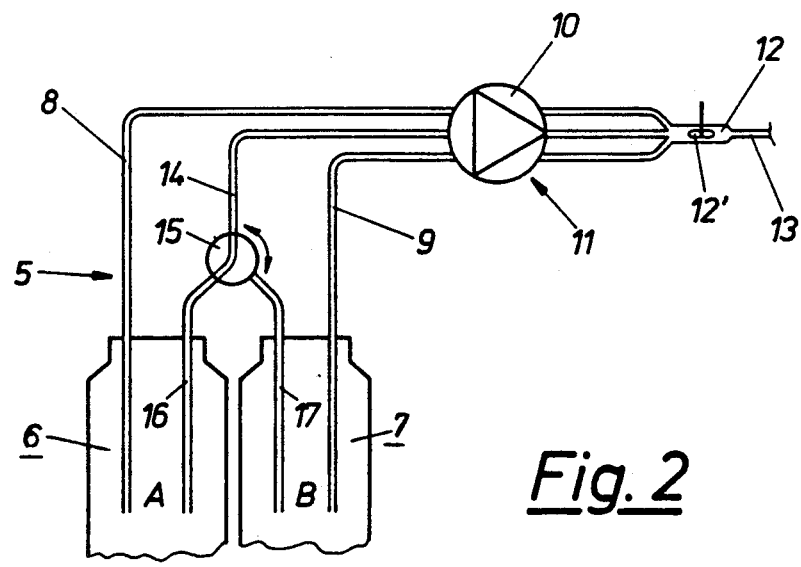
FIGS. 2 to 4 present further variants of this arrangement.

In the arrangement presented in FIG. 2 a third piece of tubing, 14 is added to the pieces 8 and 9, which piece 14 may be connected via hoses 16 and 17 to the storage containers 6 and 7 in turn by means of a switching unit 15. If identical cross-sections are selected for the three pieces of tubing 8,9,14, the mixing ratio may be inverted from 1:2 to 2:1 by operating the switching unit 15.

Figure 3:
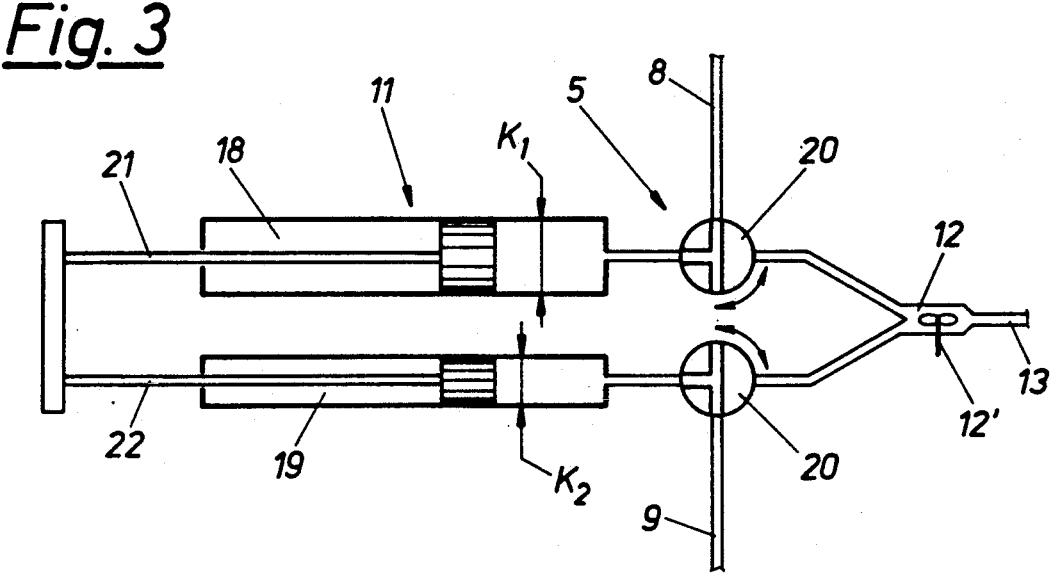

FIG. 3 shows another variant in which the mixing ratio can be adjusted most accurately by means of two syringes 18 and 19. These syringes carry valves 20 which are switched over between suction phase and expulsion phase. The mixing ratio is defined by the different cross-sections $K_1$ and $K_2$ of the two syringes 18 and 19.

Figure 4:
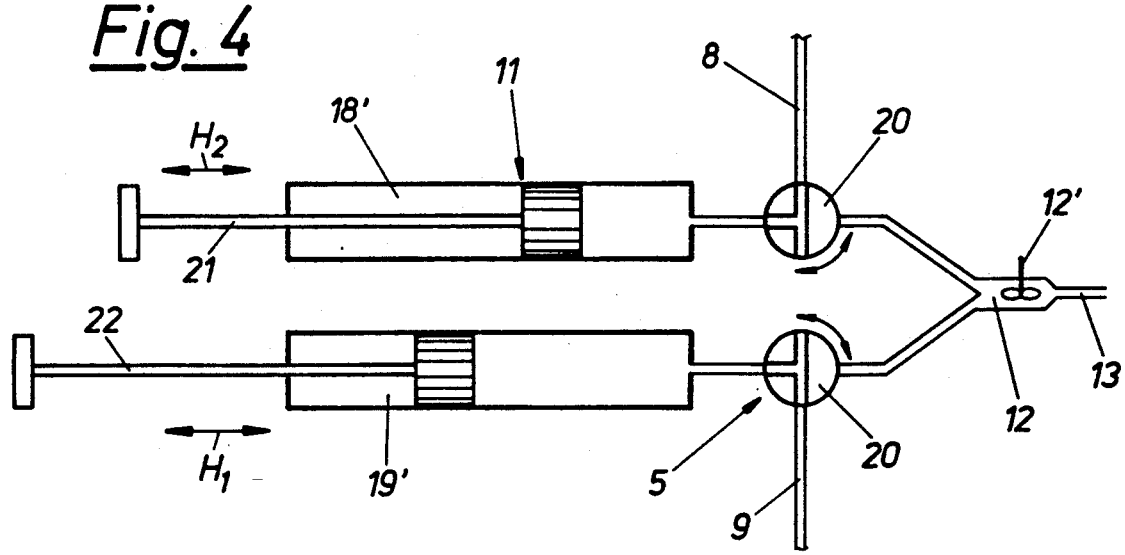

As shown in FIG. 4 it is also possible to have different stroke lengths $H_1$ and $H_2$ for plungers 18' and 19' of identical cross-sections. The two plungers 21, 22, which have a common actuating mechanism in the variant of FIG. 3, are actuated independently of each other in FIG. 4, for instance by stepping motors not shown here.

We claim:

1. A method of calibrating a measurement apparatus that contains measuring electrodes and can be used to determine the pH and $pCO_2$ values of aqueous sample media, said method comprising the steps of providing two aqueous base solutions A and B which will react with one another when mixed but which will remain stable with respect to $CO_2$ content when exposed to ambient air, storing said two aqueous base solutions A and B in separate storage containers, mixing said base solutions A and B at a predetermined ratio such that they will react and form a calibration liquid having predetermined pH and $pCO_2$ values, immediately passing said calibration liquid to said measurement apparatus so as to contact said measuring electrodes, and taking calibration readings from said measuring electrodes, wherein said base solution A contains an acid component of a pH buffer system and said base solution B contains carbonate and bicarbonate, wherein a $pCO_2$ value resulting from the bicarbonate/carbonate ratio is obtained in said base solution B, which corresponds to a mean $pCO_2$ value of ambient air.

2. A method according to claim 1, wherein said base solution B additionally contains an alkaline component of said pH buffer system.

3. A method according to claim 1, wherein a $pCO_2$ value resulting from the bicarbonate/carbonate ratio is obtained in said base solution B, which corresponds to a mean $pCO_2$ value of ambient air.

4. A method according to claim 1, wherein inactive salts are added to at least one of said base solutions A and B, in order to adapt ionic strength to that of said aqueous sample media.

5. A method according to claim 3, wherein inactive salts are added to at least one of said base solutions A and B, in order to adapt ionic strength to that of said aqueous sample media.

6. A method according to claim 4, wherein at least one salt of a group consisting of NaCl and KCl is used as said pH inactive salt.

7. A method according to claim 1, wherein said pH buffer system is selected from a group of phosphate buffers and water-soluble organic amino buffers.

8. A method according to claim 1, wherein at least a two-point calibration is carried out, for which calibration at least two different mixing ratios of said base solutions A and B are selected.

9. A method according to claim 8, wherein said two selected mixing ratios are reciprocals.

10. A method according to claim 9, wherein said two selected mixing ratios are 1:2 and 2:1.

11. A method according to claim 1, wherein a dye is added to one of said base solutions A and B and wherein said mixing ratio of said base solutions is tested by means of optical methods, such as absorption measurements.

12. A method according to claim 1, wherein one of said base solutions A and B is equilibrated with oxygen from ambient air immediately before calibration, and wherein a $pO_2$ calibration is carried out in addition to said pH and $pCO_2$ calibrations.

13. A method according to claim 12, wherein equilibration of one of said base solutions A and B with oxygen is performed in a piece of silicone tubing between a storage container of said respective base solution and said corresponding measuring electrodes.

14. A method according to claim 13, wherein for zero point calibration of $pO_2$, oxygen is removed from one of said base solutions A and B by a cathodic reaction.

15. A method according to claim 13, wherein for zero point calibration of $pO_2$ a solution C is used which contains an oxygen-reducing agent.

16. A method according to claim 15, wherein said oxygen content of said solution C used for zero point calibration of $pO_2$ is checked by adding a redox indicator, wherein color of said redox indicator changes upon transition from oxidized to reduced state.

17. A method according to claim 15, wherein said oxygen-reducing agent is $Na_2SO_3$ and wherein said oxygen content of said solution C is checked by adding a pH indicator which will undergo a change in color when the pH of said solution C is shifted from 9 to 7.

* * * * *